United States Patent
Nakai

(12) 
(10) Patent No.: US 11,559,269 B2
(45) Date of Patent: Jan. 24, 2023

(54) X-RAY IMAGING APPARATUS, MEDICAL INFORMATION PROCESSING APPARATUS, X-RAY DETECTOR, AND CORRECTION METHOD OF X-RAY DETECTOR

(71) Applicant: Canon Medical Systems Corporation, Otawara (JP)

(72) Inventor: Hiroaki Nakai, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 256 days.

(21) Appl. No.: 16/987,749

(22) Filed: Aug. 7, 2020

(65) Prior Publication Data

US 2021/0052236 A1 Feb. 25, 2021

(30) Foreign Application Priority Data

Aug. 20, 2019 (JP) .............................. JP2019-150288

(51) Int. Cl.
| | |
|---|---|
| A61B 6/00 | (2006.01) |
| G01T 1/24 | (2006.01) |
| G06N 5/04 | (2006.01) |
| G06T 11/00 | (2006.01) |
| G06N 20/00 | (2019.01) |
| A61B 6/03 | (2006.01) |
| G06N 3/04 | (2006.01) |

(52) U.S. Cl.
CPC ............ *A61B 6/4233* (2013.01); *A61B 6/032* (2013.01); *A61B 6/4241* (2013.01); *A61B 6/4452* (2013.01); *A61B 6/58* (2013.01); *G01T 1/247* (2013.01); *G06N 5/04* (2013.01); *G06N 20/00* (2019.01); *G06T 11/008* (2013.01); *G01T 1/249* (2013.01); *G06N 3/0454* (2013.01); *G06T 2210/41* (2013.01)

(58) Field of Classification Search
CPC ..... A61B 6/032; A61B 6/4233; A61B 6/4241; A61B 6/4452; A61B 6/58; G01T 1/247; G01T 1/249; G06N 3/006; G06N 3/0454; G06N 3/088; G06N 5/04; G06N 20/00; G06T 11/008; G06T 2210/41
See application file for complete search history.

(56) References Cited

U.S. PATENT DOCUMENTS

| | | | |
|---|---|---|---|
| 4,368,536 A | 1/1983 | Pfeiler | |
| 5,757,227 A * | 5/1998 | McQuaid | ................ H03F 3/082 327/557 |
| 8,450,693 B2 | 5/2013 | Stearns | |

(Continued)

*Primary Examiner* — Mark R Gaworecki
(74) *Attorney, Agent, or Firm* — Oblon, McClelland, Maier & Neustadt, L.L.P.

(57) ABSTRACT

In general, an X-ray imaging apparatus according to one embodiment includes an X-ray tube, an X-ray detector, and processing circuitry. The processing circuitry is configured to obtain correction-target data that includes component deterioration resulting from a transient response of the X-ray detector, and to output, based on the obtained correction-target and a model that outputs data in which component deterioration resulting from a transient response is reduced based on an input of data that includes component deterioration resulting from a transient response, corrected data in which the component deterioration resulting from the transient response of the X-ray detector is reduced.

20 Claims, 9 Drawing Sheets

(56) References Cited

U.S. PATENT DOCUMENTS

| | | | |
|---|---|---|---|
| 2009/0129538 A1* | 5/2009 | Tkaczyk | G01T 1/249 250/361 R |
| 2016/0299002 A1* | 10/2016 | Steadman Booker | G01T 1/17 |
| 2018/0180765 A1 | 6/2018 | Teague et al. | |
| 2018/0329086 A1* | 11/2018 | Roessl | G01T 1/2928 |
| 2020/0222024 A1* | 7/2020 | Edic | G01N 23/046 |

* cited by examiner

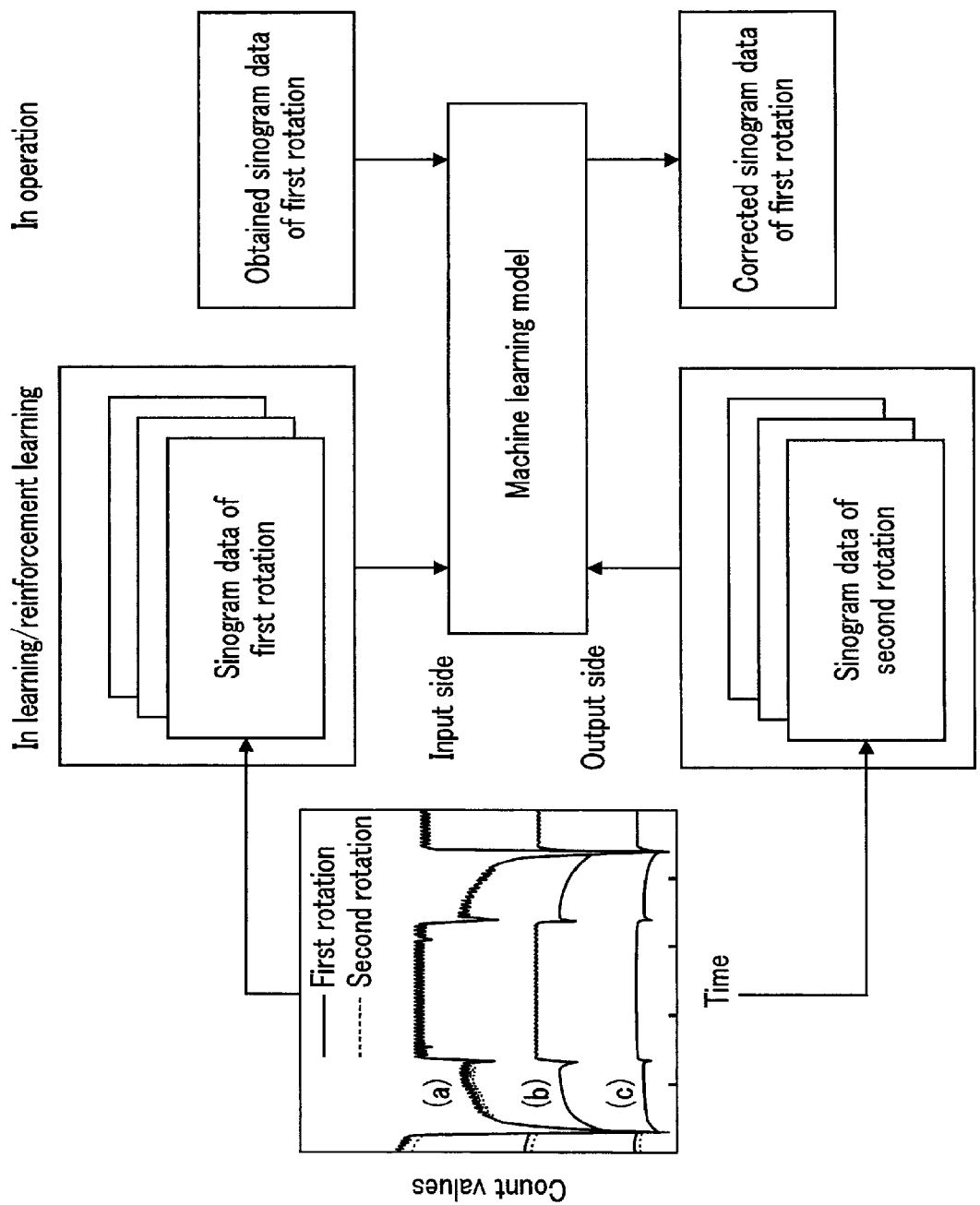
F I G. 6

X-RAY IMAGING APPARATUS, MEDICAL INFORMATION PROCESSING APPARATUS, X-RAY DETECTOR, AND CORRECTION METHOD OF X-RAY DETECTOR

CROSS-REFERENCE TO RELATED APPLICATIONS

This application is based upon and claims the benefit of priority from the Japanese Patent Application No. 2019-150288, filed Aug. 20, 2019, the entire contents of which are incorporated herein by reference.

FIELD

Embodiments described herein relate generally to an X-ray imaging apparatus, a medical information processing apparatus, an X-ray detector, and a correction method of an X-ray detector.

BACKGROUND

As semiconductor materials for X-ray detectors (e.g., photon counting detector), compound semiconductors, such as cadmium telluride (CdTe) and cadmium zinc telluride (CdZnTe; CZT), are used in some cases. It is known that X-ray detectors using these compound semiconductors have instability in their response to fluctuations in incident X-rays. In other words, an output of such X-ray detectors may contain deteriorated components resulting from a transient response such as overshoot and undershoot. When an image is reconstructed from a detector output that includes such deteriorated components, there is a problem wherein CT values of the reconstructed image may deviate from correct values.

BRIEF DESCRIPTION OF THE DRAWINGS

FIG. 6 is a diagram for explaining an example of a machine learning model according to a fourth modification.

DETAILED DESCRIPTION

In general, according to one embodiment, an X-ray imaging apparatus includes an X-ray tube, an X-ray detector, and processing circuitry. The X-ray tube generates X-rays. The X-ray detector detects X-rays generated by the X-ray tube and passing through a subject. The processing circuitry is configured to obtain correction-target data that includes component deterioration resulting from a transient response of the X-ray detector, and to output, based on the obtained correction-target and a model that outputs data in which component deterioration resulting from a transient response is reduced based on an input of data that includes component deterioration resulting from a transient response and data corrected data in which the component deterioration resulting from the transient response of the X-ray detector is reduced.

Hereinafter, an X-ray imaging apparatus, a medical information processing apparatus, an X-ray detector, and a correction method of an X-ray detector will be explained with reference to the drawings. In the descriptions hereinafter, constituent elements having the same or almost the same functions will be denoted by the same reference symbols, and a duplicate description will be made only when required. Where the same element is illustrated in different drawings, the dimensions and scales may be different between the drawings.

In the present embodiment, an X-ray computed tomography apparatus capable of performing photon counting CT (PCCT) will be described as an example of the X-ray imaging apparatus. The technique according to the present embodiment is applicable not only to an X-ray computed tomography apparatus but also to a SPECT and an X-ray diagnostic apparatus.

The X-ray computed tomography apparatus (CT apparatus) may be of various types, such as third generation CT and fourth generation CT, and either type can be applied to the present embodiment. Herein, the third generation CT is a "rotate/rotate-type" in which an X-ray tube and a detector are integrally rotated around a subject. The fourth generation CT is a "stationary/rotate-type" in which multiple X-ray detection elements are arrayed in a ring shape, and only an X-ray tube is rotated around a subject.

Figure 1:
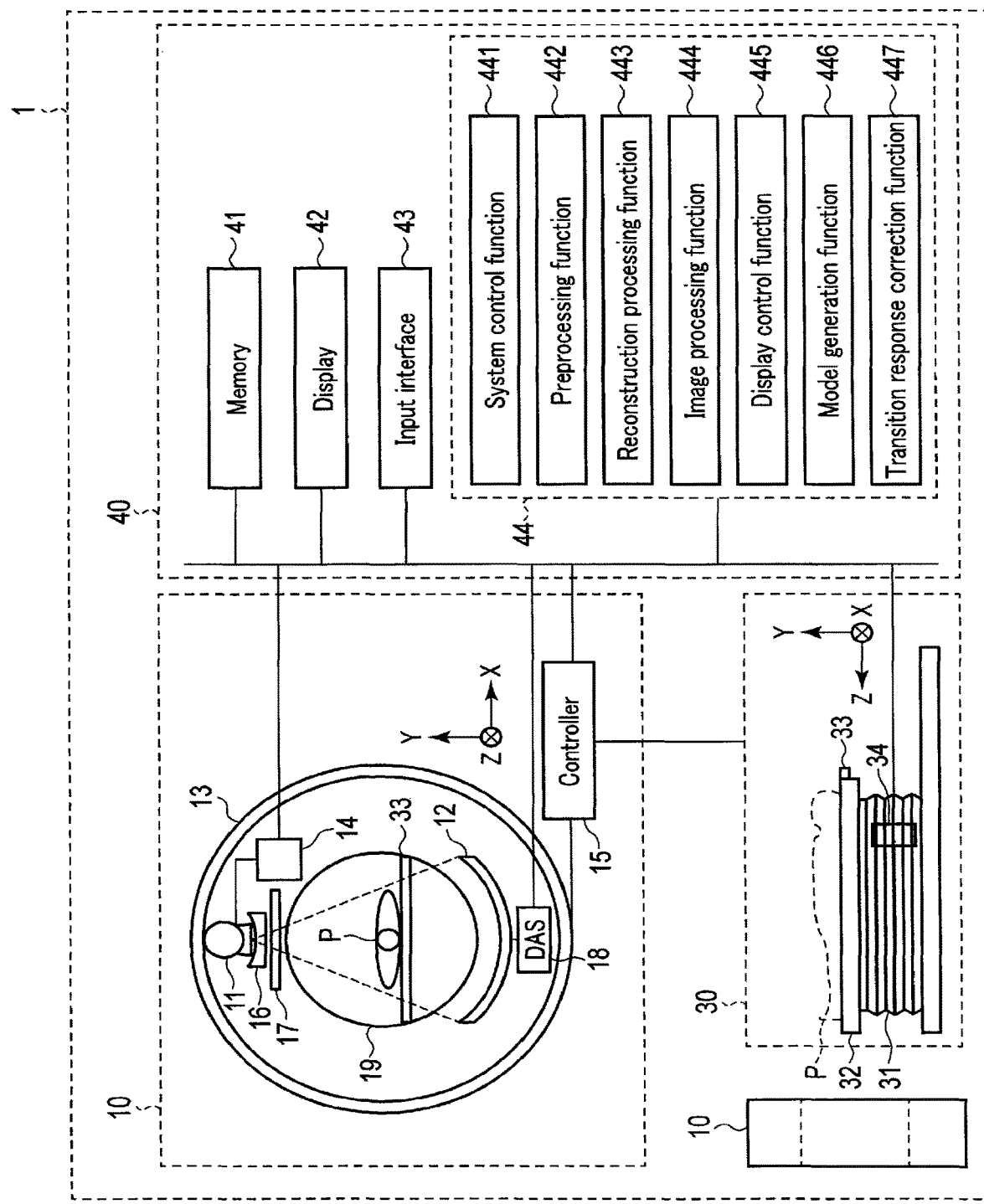
FIG. 1 is a diagram showing an example of a configuration of an X-ray computed tomography apparatus according to an embodiment.

FIG. 1 is a diagram showing an example of a configuration of the X-ray computed tomography apparatus according to an embodiment. In the X-ray computed tomography apparatus 1, X-rays are radiated on a subject P from an X-ray tube 11, and the radiated X-rays are detected by an X-ray detector 12. Based on the output from the X-ray detector 12, the X-ray computed tomography apparatus 1 generates a CT image relating to the subject P.

As illustrated in FIG. 1, the X-ray computed tomography apparatus 1 includes a gantry 10, a bed 30 and a console 40. FIG. 1 illustrates a plurality of gantries 10 for convenience of explanation. The gantry 10 is a scan device including a configuration for X-ray CT scan of the subject P. The bed 30 is a conveyance device for placing thereon the subject P that is the target of an X-ray CT scan and for positioning the subject P. The console 40 is a computer which controls the gantry 10. For example, the gantry 10 and bed 30 are installed in a CT examination room, and the console 40 is installed in a control room adjacent to the CT examination room. The gantry 10, bed 30 and console 40 are communicably connected by wire or wirelessly. Note that the console 40 may not necessarily be installed in the control room. For example, the console 40 may be installed in the same room as the gantry 10 and bed 30. Alternately, the console 40 may be integrated into the gantry 10.

As illustrated in FIG. 1, the gantry 10 includes the X-ray tube 11, the X-ray detector 12, a rotation frame 13, an X-ray high voltage generator 14, a control device 15, a wedge 16, a collimator 17, and data acquisition circuitry (data acquisition system; DAS) 18.

The X-ray tube 11 radiates X-rays on the subject P. Specifically, the X-ray tube 11 includes a cathode which generates thermions, an anode which receives the thermions flying from the cathode and generates X-rays, and a vacuum tube which holds the cathode and anode. The X-ray tube 11 is connected to the X-ray high voltage generator 14 via a high-voltage cable. A tube voltage is applied between the cathode and anode by the X-ray high voltage generator 14. By the application of the tube voltage, thermions fly from the cathode toward the anode. By the thermions flying from the cathode toward the anode, a tube current flows. By the application of high voltage and the supply of filament current from the X-ray high voltage generator 14, thermions fly from the cathode (filament) toward the anode (target), and X-rays are generated by the thermions impinging on the anode. For example, the X-ray tube 11 may be a rotating-anode-type X-ray tube which generates X-rays by radiating thermions on a rotating anode.

The hardware for generating X-rays is not limited to the X-ray tube 11. For example, a fifth generation system may be used for generating X-rays without the X-ray tube 11. The fifth generation system includes a focus coil which focuses an electron beam generated from an electron gun, a deflection coil which electromagnetically deflects it, and a target ring which surrounds the half circumference of the subject P and generates an X-ray by collision of a deflected electron beam thereon.

The X-ray detector 12 detects X-rays that have been generated from the X-ray tube 11 and have passed through the subject P. In the X-ray detector 12, a plurality of X-ray detection elements arranged in a two-dimensional manner are mounted. The X-ray detector 12 is typically realized by a direct detection-type semiconductor detector. Each X-ray detection element detects an X-ray photon from the X-ray tube 11, and generates an electrical pulse (electric signal, detection signal) in accordance with the energy of the detected X-ray photon. Specifically, the X-ray detection element is comprised of a semiconductor diode made of a pair of electrodes provided at the ends of the semiconductor. The X-ray photon incident to the semiconductor is converted into an electron-and-hole pair. The number of electron-and-hole pairs generated by incidence of a single X-ray photon is dependent on the energy of the incident X-ray photon. An electron and a positive hole are attracted to the pair of electrodes formed on the ends of the semiconductor. The pair of electrodes generates an electric pulse having a peak value in accordance with the electric charge of the electron-and-hole pair. A single electric pulse has a peak value in accordance with the energy of the incident X-ray photon. As the semiconductor materials according to the present embodiment, a material having a relatively large atomic number and capable of efficiently converting an X-ray photon into an electron-and-hole pair should be used preferably. As semiconductor materials suitable for the photon counting CT, compound semiconductors such as cadmium telluride (CdTe) and cadmium zinc telluride (CdZnTe; CZT) are known. The X-ray detector 12 according to the present embodiment is not limited to a direct detection-type semiconductor detector, and it may be an indirect detection-type semiconductor detector. As an indirect detection-type X-ray detector 12, a type using a combination of a scintillator and an optical sensor is applicable.

The rotation frame 13 is an annular frame which supports the X-ray tube 11 and X-ray detector 12 such that the X-ray tube 11 and X-ray detector 12 are rotatable around a rotational axis (Z-axis). Specifically, the rotation frame 13 supports the X-ray tube 11 and X-ray detector 12 such that the X-ray tube 11 and X-ray detector 12 are opposed to each other. The rotation frame 13 is supported on a stationary frame (not shown) such that the rotation frame 13 is rotatable around the rotational axis. The control device 15 causes the rotation frame 13 to rotate around the rotational axis by the control device 15, thereby rotating the X-ray tube 11 and X-ray detector 12 around the rotational axis. The rotation frame 13 rotates at a fixed angular velocity around the rotational axis by receiving a driving force from a driving mechanism of the control device 15. A field of view (FOV) is set in a bore 19 of the rotation frame 13.

In the present embodiment, the rotational axis of the rotation frame 13 in a non-tilt state or the longitudinal direction of the table top 33 of the bed 30 is defined as a Z-axis direction; a direction orthogonal to the Z-axis direction and horizontal to the floor surface is defined as an X-axis direction; and a direction orthogonal to the Z-axis direction and perpendicular to the floor surface is defined as a Y-axis direction.

The X-ray high voltage generator 14 includes a high voltage generation device and an X-ray control device. The high voltage generation device includes electric circuitry such as a transformer and a rectifier, and generates a high voltage which is applied to the X-ray tube 11 and a filament current which is supplied to the X-ray tube 11. The X-ray control device controls an output voltage according to an X-ray radiated from the X-ray tube 11. The high voltage generation device may adopt either a transformer method or an inverter method. The X-ray high voltage generator 14 may be provided in the rotation frame 13 in the gantry 10, or may be provided in the stationary frame (not shown) in the gantry 10.

The control device 15 controls the X-ray high voltage generator 14 and data acquisition circuitry 18 in order to perform, by processing circuitry 44 of the console 40, X-ray CT imaging in accordance with a system control function 441. The controller 15 includes processing circuitry including a CPU (central processing unit) or an MPU (micro processing unit) or the like, and a driving device such as a motor and an actuator or the like. The processing circuitry includes, as hardware resources, a processor such as a CPU, and a memory such as a ROM (read only memory) or RAM (random access memory). The controller 15 performs various functions using the processor which executes a program developed on the memory.

Each of the functions is not necessarily implemented by a single processing circuit. Processing circuitry may be configured by combining a plurality of independent processors, and the processors may execute respective programs to implement the functions.

In addition, the control device 15 may be realized by an ASIC (application specific integrated circuit) or an FPGA (field programmable gate array). Further, the control device 15 may be realized by a CPLD (complex programmable logic device) or an SPLD (simple programmable logic device).

The control device 15 has a function of controlling the operation of the gantry 10 and the bed 30 upon receipt of an input signal from an input interface 43 provided on the console 40 or the gantry 10 as described later. For example, the controller 15 performs control to rotate the rotation frame 13, control to tilt the gantry 10, or control to operate the bed 30 and the table top 33 in response to an input signal. The control to tilt the gantry 10 is implemented by the controller 15 rotating the rotation frame 13 around an axis parallel to the X-axis direction based on tilt angle information input through the input interface attached to the gantry 10.

The control device 15 may be provided in the gantry 10, or may be provided in the console 40.

The wedge 16 adjusts the dose of X-rays which are applied to the subject P. Specifically, the wedge 16 attenuates X-rays so that the dose of X-rays to be applied to the subject P from the X-ray tube 11 exhibits a predetermined distribution. For example, as the wedge 16, a metal plate of aluminum or the like, such as a wedge filter or a bow-tie filter, is used.

The collimator 17 restricts the range of radiation of X-rays which have passed through the wedge 16. The collimator 17 slidably supports a plurality of lead plates which shield X-rays, and adjusts the form of a slit which is formed by the lead plates. The collimator 17 may also be referred to as an X-ray diaphragm.

The data acquisition circuitry 18 (counter circuitry) acquires count data representing the count number of X-rays detected by the X-ray detector 12 for a plurality of energy bandwidths in accordance with a control signal from the controller 15. As a counting method of the data acquisition circuitry 18, a sinogram mode scheme and a list mode scheme are known. In the sinogram mode scheme, the data acquisition circuitry 18 performs peak discrimination on electric pulses (detection signals) from the X-ray detector 12, and individually counts, for each X-ray detection element, the number of electric pulses as the number of X-ray photons for each of the plurality of predetermined energy bandwidths. In the list mode scheme, the data acquisition circuitry 18 performs peak discrimination on electrical pulses from the X-ray detector 12, and records the peak values of the electric pulses as energy values of the X-ray photons, associating the values with time of detection. Furthermore, the data acquisition circuitry 18 refers to the record in order to sort the X-ray photons into the predetermined energy bandwidths and to count the number of X-ray photons per view for each energy bandwidth.

Hereinafter, the number of X-ray photons counted by the data acquisition circuitry 18 will be referred to as "count number". Digital data representing the count number will be referred to as "count data" (projection data). In the list mode scheme, the data acquisition circuitry 18 may be provided in the console 40 instead of being provided in the gantry 10 as mentioned previously. The data acquisition circuitry 18 is implemented, for example, by an ASIC on which a circuit element capable of generating projection data is mounted. The projection data is transmitted to the console 40 via a non-contact data transmission device or the like.

The bed 30 includes a base 31, a support frame 32, the table top 33, and a bed actuator 34. The base 31 is installed on the floor surface. The base 31 is a structure which supports the support frame 32 such that the support frame 32 is movable in the vertical direction (Y-axis direction) relative to the floor surface. The support frame 32 is a frame provided on an upper part of the base 31. The support frame 32 supports the table top 33 such that the table top 33 is slidable along the rotational axis (Z-axis). The table top 33 is a plate with flexibility on which the subject P is placed.

The bed actuator 34 is housed in the bed 30. The bed actuator 34 is a motor or an actuator which generates driving force for moving the support frame 32 and table top 33 on which the subject P is placed. The bed actuator 34 operates in accordance with the control by the console 40, etc.

The console 40 includes a memory 41, a display 42, an input interface 43, and processing circuitry 44. Data communication between the memory 41, display 42, input interface 43, and processing circuitry 44 is executed via a bus (BUS). Although the console 40 is described as a separate body from the gantry 10, the console 40 or some components of the console 40 may be included in the gantry 10.

The memory 41 is a storage device which stores various kinds of information, such as an HDD (hard disk drive), an SSD (solid state drive) or an integrated circuit storage device. The memory 41 may be, aside from the HDD, SSD or the like, a portable storage medium such as a CD (compact disc), a DVD (digital versatile disc), a Blu-Ray™ disc (BD), or a flash memory. The memory 41 may be a drive unit which reads/writes various kinds of information from/to a semiconductor memory device or the like, such as a flash memory or a RAM. Alternately, a storage area of the memory 41 may exist in the X-ray computed tomography apparatus 1, or may exist in an external storage device connected over a network. The memory 41 stores, for example, projection data and reconstructed image data. The memory 41 may store a machine learning model (learning model), for example.

The display 42 displays various kinds of information. The display 42 outputs, for instance, a medical image (CT image) generated by the processing circuitry 44, and a GUI (graphical user interface) or the like for accepting various kinds of operations from an operator. Any of various types of display may be used as the display 42 as appropriate. For example, a liquid crystal display (LCD), a cathode ray tube (CRT) display, an organic electro luminescence display (OELD), or a plasma display may be used as the display 42.

The display 42 may be arranged at any location in the control room. The display 42 may be provided on the gantry 10. The display 42 may be a desktop-type display, or may be provided as a tablet terminal or the like capable of wireless communication with the main body of the console 40. As the display 42, one or two or more projectors may be used.

The input interface 43 accepts various kinds of input operations from the operator, converts the accepted input operations to electric signals, and outputs the electric signals to the processing circuitry 44. For example, the input interface 43 receives, from the operator, an acquisition condition for projection data acquisition, a reconstruction condition for CT image reconstruction, and an image processing condition for generating a post-processing image from the CT image, etc. For the input interface 43, for example, a mouse, a keyboard, trackball, a switch, a button, a joystick, a touch pad, or a touch panel display can be used as appropriate.

In the present embodiment, the input interface 43 does not necessarily include a physical operation component such as a mouse, a keyboard, a trackball, a switch, a button, a joystick, a touch pad, or a touch panel display. Examples of the input interface 43 include processing circuitry of an electric signal, which receives an electric signal corresponding to an input operation from an external input device, which is provided separately from the apparatus, and outputs the received electric signal to the processing circuitry 44. The input interface 43 may be provided on the gantry 10. The input interface 43 may be provided as a tablet terminal or the like capable of wireless communication with the main body of the console 40.

The processing circuitry 44 controls the operation of the entirety of the X-ray computed tomography apparatus 1 in accordance with an electric signal of an input operation which is output from the input interface 43. The processing circuitry 44 includes, as hardware resources, a processor such as a CPU, an MPU, and a GPU, etc. and a memory such as a ROM, a RAM, etc. The processing circuitry 44 executes a system control function 441, a preprocessing function 442, a reconstruction processing function 443, an image processing function 444, a display control function 445, a model generation function 446, a transient response correction function 447, and the like, by the processor which executes a program developed on the memory. For example, the processing circuitry 44 according to the present embodiment performs a model generation function 446 through a model generation program. For example, the processing circuitry 44 according to the present embodiment performs a transient response correction function 447 through a transient response correction program.

Note that the processing circuitry 44 may be implemented by an ASIC, FPGA, CPLD, or SPLD.

Note that the embodiment is not limited to the case in which the respective functions 441 to 447 are enabled by single processing circuitry. Processing circuitry may be composed by combining a plurality of independent processors, and the respective processors may execute programs, thereby realizing the functions 441 to 447.

In the system control function 441, the processing circuitry 44 controls the X-ray high voltage generator 14, control device 15 and data acquisition circuitry 18 in order to execute an X-ray CT scan. The processing circuitry 44 obtains projection data (count data) output from the data acquisition circuitry 18.

In the preprocessing function 442, the processing circuitry 44 applies preprocesses, such as a logarithmic conversion process, an offset correction process, an inter-channel sensitivity correction process, an inter-channel gain correction process, a pile-up correction process, a response function correction process, and beam hardening correction, to the projection data which is output from the data acquisition circuitry 18.

In the reconstruction processing function 443, the processing circuitry 44 applies reconstruction processing, which uses a filtered back projection method, an iterative approximation reconstruction method, or machine learning, to the projection data preprocessed by the preprocessing function 442, thereby generating a CT image.

Herein, the projection data generated from a counting result obtained through the photon counting CT includes information regarding the energy of X-rays attenuated as a result of passing through the subject P. For this reason, the processing circuitry 44 may generate CT image data of all energy components by adding information of all bins for each pixel, or CT image data of a specific energy component, or CT image data of each energy component.

The processing circuitry 44 may allocate a color tone to each pixel of CT image data of each energy component in accordance with the energy component, and generate image data by multiplexing a plurality of CT image data sets which are color-coded according to the energy components. The processing circuitry 44 may generate image data that allows identification of materials through utilization of a K absorption edge unique to each material, for example. Other types of image data generated by the processing circuitry 44 may be single-color X-ray image data, density image data, or effective atomic number image data, for example.

There is a technique of distinguishing types, abundance, density, and the like of materials included in the subject P (material decomposition) through utilizing different X-ray absorption characteristics varying among the materials. For example, the processing circuitry 44 can reconstruct a material decomposition image using material decomposition information obtained by the material decomposition performed on projection data.

In the image processing function 444, the processing circuitry 44 converts the CT image, which is generated by the reconstruction processing function 443, to cross section image data of an arbitrary cross section or rendered image data from an arbitrary viewpoint direction. The conversion is performed based on an input operation which was accepted from the operator via the input interface 43. For example, the processing circuitry 44 applies three-dimensional image processing, such as volume rendering, surface rendering, image value projection processing, multi-planar reconstruction (MPR) processing or curved MPR (CPR) processing to the CT image data, thereby generating rendered image data from an arbitrary viewpoint direction. Such generation of rendered image data from an arbitrary viewpoint direction may be performed directly by the reconstruction processing function 443.

In the display control function 445, the processing circuitry 44 causes the display 42 to display an image based on various kinds of image data generated by the image processing function 444. Images to be displayed on the display 42 include: a CT image based on CT image data, a cross section image based on cross section image data of an arbitrary cross section, and a rendered image from an arbitrary viewpoint direction based on rendered image data from the arbitrary viewpoint direction. Further, images to be displayed on the display 42 include an image for displaying an operation screen.

The processing circuitry 44, through the model generation function 446, obtains a series of time-series data including an influence of a transient response of the X-ray detection elements, in other words, a series of time-series data including component deterioration resulting from the transient response of the X-ray detector 12. The processing circuitry 44 generates data regarding a period that includes a period in which a transient response of the X-ray detector 12 occurs ("first period") and data regarding a period after the first period that includes a period in which the transient response of the X-ray detector 12 is converged ("second period"), based on the obtained series of time-series data. In other words, the data regarding the first period is data that includes component deterioration resulting from a transient response of the X-ray detector 12. The data regarding the second period is data that does not include component deterioration resulting from a transient response of the X-ray detector 12, or data in which component deterioration resulting from a transient response of the X-ray detector 12 is insignificant. The processing circuitry 44 associates the data regarding the first period (input-side learning data) with the data regarding the second period (output-side learning data) so as to generate a learning data set for the machine learning model (learning model). The processing circuitry 44 conducts learning and/or reinforcement learning of the machine learning model through a use of the generated learning data set. The processing circuitry 44 that enables the model generation function 446 is an example of an acquisition unit, a generation unit, and a processing unit.

The generation of a learning data set and the learning and/or reinforcement learning of a machine learning model may be conducted externally to the processing circuitry 44, for example a work station provided externally to the X-ray computed tomography apparatus 1. In this case, preferably the learned machine learning model is stored in the memory 41.

The processing circuitry 44 obtains, through the transient response correction function 447, data targeted for correction (input data). Herein, the data targeted for correction is data that includes an influence of a transient response of the X-ray detection elements, namely data that includes component deterioration resulting from a transient response of the X-ray detector 12. The processing circuitry 44 generates corrected data (output data) in which the component deterioration resulting from a transient response has been reduced, based on the learned machine learning model and the obtained correction target data. The processing circuitry 44 that enables the transient response correction function 447 is an example of an acquisition unit and a processing unit.

Although the console 40 as a single console executes a plurality of functions in the above description, a plurality of functions may be executed by different consoles. For example, the functions of the processing circuitry 44, such as the pre-processing function 442, the reconstruction function 443, the model generation function 446, and the transient response correction function 447, may be distributed.

The processing circuitry 44 may not necessarily be included in the console 40, and may be included in an integrated server which collectively performs processing on detection data obtained by a plurality of medical diagnostic imaging apparatuses.

The post-processing may be performed by the console 40 or an external workstation. It may also be performed by both the console 40 and the external workstation at the same time.

The technique according to the present embodiment is applicable to a single-tube-type X-ray computed tomography apparatus, as well as a so-called multi-tube-type X-ray computed tomography apparatus in which a plurality of pairs of X-ray tubes and X-ray detectors are mounted on rotary rings.

The technique according to the present embodiment is applicable to the X-ray computed tomography apparatus 1 capable of performing dual energy imaging. At this time, the X-ray high-voltage apparatus 14 can switch the energy spectrum of X-rays emitted from the X-ray tube 11 through high-speed switching between two voltage values, for example. In other words, the X-ray computed tomography apparatus 1 is configured to acquire projection data from each acquisition view, while modulating a tube voltage at a timing in accordance with a control signal for tube voltage modulation. By imaging a subject with different tube voltages, it is possible to improve gray-scale contrast in a CT image based on energy transmissivity of materials of each X-ray energy spectrum.

Figure 2:
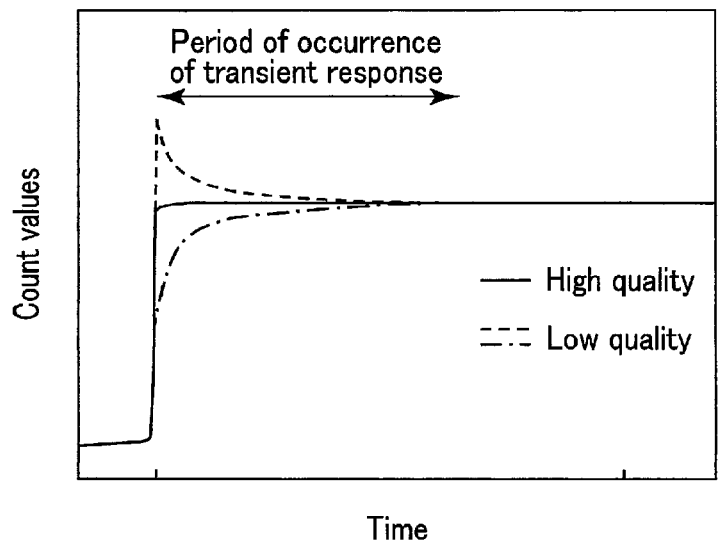
FIG. 2 is a diagram for explaining transient response characteristics of an X-ray detector shown in FIG. 1.

FIG. 2 is a diagram for explaining transient response characteristics of the X-ray detector 12 shown in FIG. 1. In the graph shown in FIG. 2, the horizontal axis represents time, and the vertical axis represents a count value. In the X-ray detector 12, a plurality of X-ray detection elements (pixels) are provided. It is preferable to acquire a stepwise output for a stepwise X-ray input for all the X-ray detection elements, as indicated by the solid line in FIG. 2. However, the output of the X-ray detector using a compound semiconductor such as CdTe or CZT may include component deterioration resulting from a transient response. For example, a low-quality X-ray detection element may exhibit an overshoot transient response to the stepwise X-ray input, as indicated by the dotted line in FIG. 2. Similarly, a low-quality X-ray detection element may exhibit an undershoot transient response to the stepwise X-ray input, as indicated by the alternate long and short dashed line in FIG. 2.

When image reconstruction is performed based on an output of the X-ray detector 12 that includes component deterioration resulting from a transient response, a CT value may not be correctly calculated in the reconstructed image. For example, a CT value of water, which should be 0, may be calculated to be an incorrect value, for example 10. For example, in terms of bones, if a value deviates from an original CT value and is calculated to be a smaller value, the bone may appear to be a light bone in the reconstructed image. For example, in terms of a contrast agent, if a value deviates from an original CT value and is calculated to be a smaller value, the concentration of the contrast agent may appear to be lighter in the reconstructed image. Despite these situations, from the viewpoint of manufacturing cost for example, it is difficult to realize an X-ray detector 12 consisting of high-quality X-ray detection elements having a sufficiently small transient response. Furthermore, from the viewpoint of exposure of subjects, it is difficult to extend a scan time in order not to use data that includes component deterioration resulting from a transient response and to further obtain scan data after a transient response converges.

Furthermore, each of the X-ray detection elements has unique transient response characteristics. The transient response characteristics vary depending on an imaging condition or an imaging target, for example. For these reasons, it is difficult to produce a correction function model for various imaging conditions and imaging targets for each of the X-ray detection elements.

In consideration of such difficulties, the X-ray computed tomography apparatus 1 according to the present embodiment corrects obtained data that includes component deterioration resulting from a transient response, using a machine learning model. The machine learning model is a composite function with a parameter in which data (input data) that includes component deterioration resulting from a transient response is input and the parameter is learned so as to output corrected data (output data, an outcome) in which the component deterioration resulting from a transient response is reduced. The composite function with a parameter is defined by a combination of a plurality of adjustable functions and parameters. The parameter is a generic term for a weighting matrix and a bias. The machine learning model is a composite function with a parameter, such as a deep neural network (DNN) or a deep convolutional neural network (DCNN). The machine learning model is recorded in, for example, the memory 41.

Herein, the operation of the X-ray computed tomography apparatus 1 according to the present embodiment will be described in detail with reference to the drawings.

Figure 3:
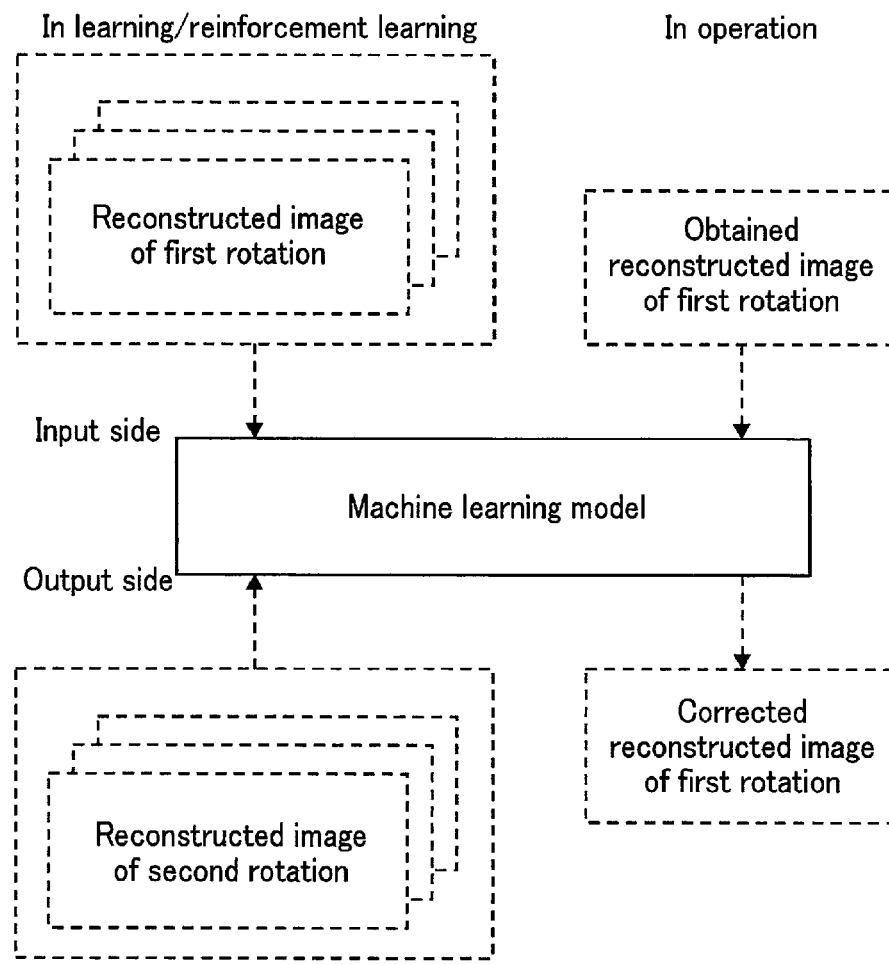
FIG. 3 is a diagram for explaining an example of a machine learning model according to the embodiment.
Figure 4:
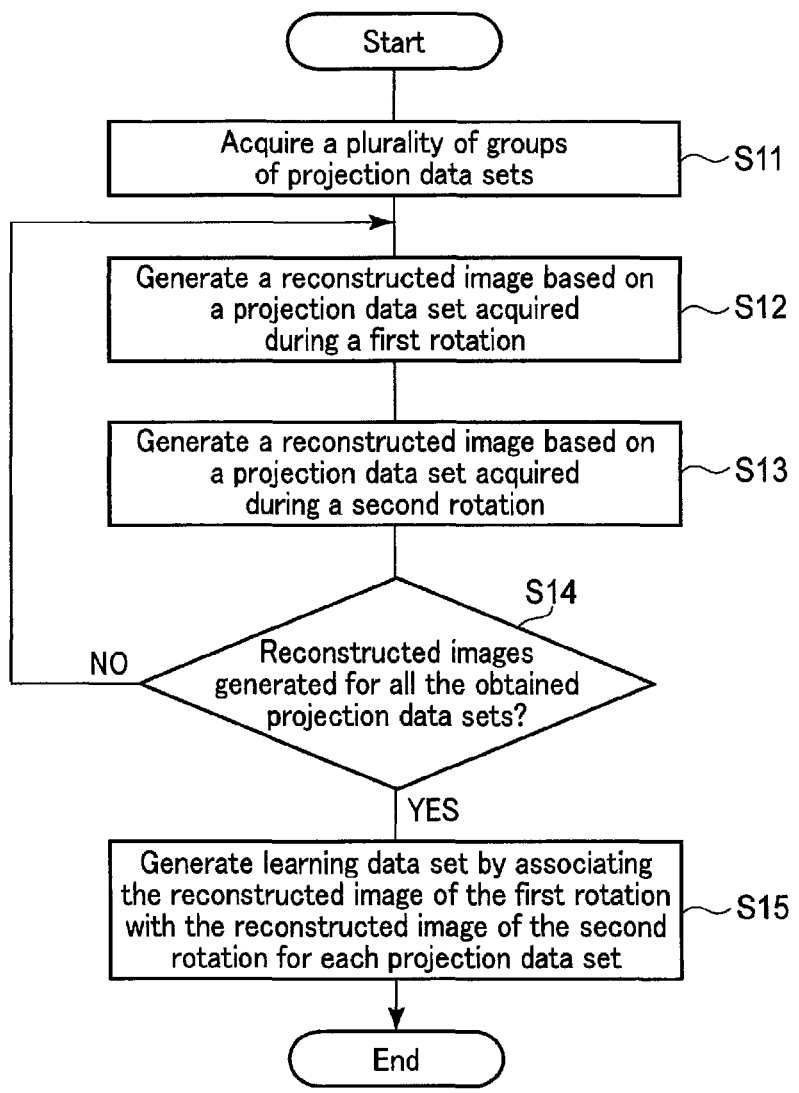
FIG. 4 is a flowchart showing an example of a flow of generation of a learning data set for the machine learning model shown in FIG. 3.

FIG. 3 is a diagram for explaining an example of a machine learning model according to the present embodiment. In the example shown in FIG. 3, the information input to and output from the machine learning model in learning and/or reinforcement learning and in operation is shown. FIG. 4 is a flowchart showing an example of a flow of generation of a learning data set for the machine learning model shown in FIG. 3.

In the present embodiment, assume that a set of learning data (input-side and output-side learning data) generated from a single group of projection data sets is a set of reconstructed images. In this case, the component deterioration resulting from a transient response is noise, etc. included in the reconstructed image, for example.

The X-ray detector 12 using a compound semiconductor, such as CdTe or CZT, exhibits a transient response in a short time elapsed from the start of the X-ray detection. The timing of the start of X-ray incidence is a timing at which a mechanical shutter opens, for example. For this reason, in the present embodiment, it is assumed that an output of the X-ray detection elements includes an influence of a transient response (component deterioration) from the start of the X-ray detection (for example, a first rotation) until a predetermined length of time (a period of time during which a transient response occurs) has elapsed, and an output of the X-ray detection elements does not include an influence of a transient response (component deterioration) after a predetermined length of time (a period of time during which a transient response occurs) has elapsed (for example, a second rotation). In other words, in the present embodiment, the reconstructed image generated based on the projection data of the first rotation is data that includes component deterioration resulting from a transient response of the X-ray detector 12, and the reconstructed image generated based on the projection data of the second rotation is data that does not include component deterioration resulting from a transient response of the X-ray detector 12.

In the present embodiment, for brevity of description, assume that a learning data set is generated by the processing circuitry 44 of the X-ray computed tomography apparatus 1.

In step S11, the processing circuitry 44 that enables the system control function 441 obtains multiple groups of projection data set from the memory 41 or an external database, for example. Each obtained group of projection data sets is a group of time-series projection data (a series of time-series data) regarding multiple views included in a predetermined period of time (for example, one rotation).

Each projection data set (typically, a first rotation projection data set) includes component deterioration belonging to projection data acquired during a period in which a transient response occurs, and normal components belonging to projection data acquired during a period after the period of occurrence of transient response.

Each projection data set (typically, a second rotation projection data set) does not include component deterioration belonging to projection data acquired during a period in which a transient response occurs, and includes normal components belonging to projection data acquired during a period after the period of occurrence of transient response.

Hereinafter, assume that each group of projection data sets includes a projection data set acquired in the first rotation and a projection data set acquired in the second rotation.

In step S12, the processing circuitry 44 that enables the reconstruction processing function 443 generates a reconstructed image of the first rotation based on the projection data set acquired in the first rotation. Herein, the reconstructed image of the first rotation is a reconstructed image that includes component deterioration resulting from a transient response.

In step S13, the processing circuitry 44 that enables the reconstruction processing function 443 generates a reconstructed image of the second rotation based on the projection data set acquired in the second rotation.

In step S14, the processing circuitry 44 that enables the model generation function 446 determines whether or not a reconstructed image is generated in step S12 and step S13 for each of the projection data sets obtained in step S11. After the flow of steps S12 and S13 is performed for all the projection data sets, the processing proceeds to step S14.

In step S15, the processing circuitry 44 that enables the model generation function 446 associates, for each projection data set, the reconstructed image of the first rotation with the reconstructed image of the second rotation as a pair of input-side learning data and output-side learning data to generate a learning data set.

The flow of the processing shown in FIG. 4 is merely an example. For example, the order of steps S12 and S13, or the order of steps S14 and S15, may be inverted.

The machine learning model may be learned through learning and/or reinforcement learning, using the generated learning data set, as shown in FIG. 3. Assume that the learning of the machine learning model is conducted for each image target (body part) and/or imaging condition.

Figure 5:
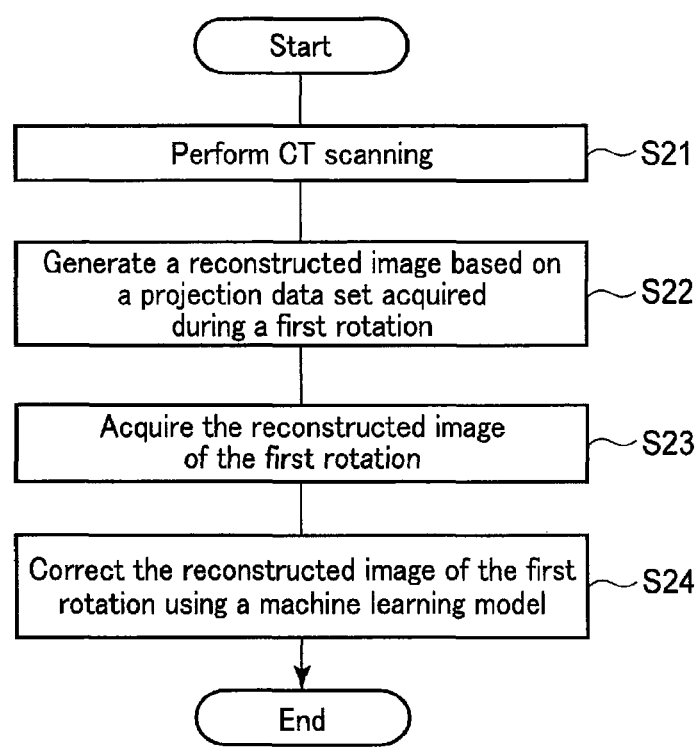
FIG. 5 is a flowchart showing an example of transient response correction using the machine learning model shown in FIG.

FIG. 5 is a flowchart showing an example of a flow of a process of correcting an output that includes a transient response using the machine learning model shown in FIG. 3.

In step S21, the processing circuitry 44 that enables the system control function 441 performs CT scanning. The processing circuitry 44 obtains projection data set output from the data acquisition circuitry 18.

In step S22, the processing circuitry 44 that enables the reconstruction processing function 443 generates a reconstructed image of the first rotation based on the projection data set acquired in the first rotation.

In step S23, the processing circuitry 44 that enables the transient response correction function 447 obtains the reconstructed image of the first rotation (data targeted for correction).

In step S24, the processing circuitry 44 that enables the transient response correction function 447 outputs a reconstructed image (corrected data) in which component deterioration resulting from a transient response of the X-ray detector is reduced, based on the learned machine learning model and the reconstructed image of the first rotation obtained in step S23.

As described above, according to the technique according to the present embodiment, even when X-ray detection elements exhibiting a transient response are used, it is possible to reduce deterioration resulting from the transient response in an X-ray detector output. Furthermore, a set of learning data is generated from a single projection data set. For this reason, there is an advantageous effect of negating a need to consider a correspondence of pixels between the input-side learning data and the output-side learning data when a learning data set is generated.

MODIFICATIONS

Hereinafter, an X-ray imaging apparatus, a medical information processing apparatus, an X-ray detector, and a correction method of an X-ray detector according to each modification will be explained with reference to the drawings. Differences from the embodiment will be mainly described here. Note that in the following description, the same reference numerals denote constituent elements having the same or almost the same functions as those of the already-described constituent elements, and a duplicate description will be made only when required.

First Modification

As a model that outputs data in which component deterioration resulting from a transient response is reduced based on an input of data that includes component deterioration resulting from a transient response, a look up table (LUT) may be used instead of a machine learning model. Even with such a configuration, the same advantageous effects as those of the above-described embodiment can be achieved.

Second Modification

As a model that outputs data in which component deterioration resulting from a transient response is reduced based on an input of data that includes component deterioration resulting from a transient response, a model generated by parameter fitting, such as linear regression or non-linear regression analysis, may be used. Even with such a configuration, the same advantageous effects as those of the above-described embodiment can be achieved.

Third Modification

A set of learning data (input-side and output-side learning data) and input data is not limited to a reconstructed image, and it may be detection signals output from the X-ray detector 12 or scano data generated based on the detection signals. Herein, a case where the detection signals are used as learning data and input data will be described as an example.

The processing circuitry 44 that enables the model generation function 446 obtains, from the data acquisition circuitry 18, time-series data (a series of time-series data) of detection signals sent from the X-ray detector 12 before being counted. The processing circuitry 44 generates a set of learning data for each piece of obtained time-series data of the detection signals. The processing circuitry 44 that enables the transient response correction function 447 obtains time-series data of detection signals that include component deterioration resulting from a transient response of the X-ray detector 12 before being counted (data targeted for correction) from the data acquisition circuitry 18, and corrects the data using the machine learning model. The counting function of the data acquisition circuitry 18 or the processing circuitry 44 generates count data (projection data) based on the time-series data of the detection signals corrected by the transient response correction function 447.

Typically, the input-side learning data and the input data is detection signals acquired in a first rotation, and the output-side learning data is detection signals acquired in a second rotation. Herein, the detection signals acquired in the first rotation are data that includes an influence of a transient response of the X-ray detection elements, which includes component deterioration belonging to the detection signals acquired during a period in which a transient response occurs, and normal components belonging to the detection signals acquired after the period of occurrence of transient response. The detection signals acquired in the second rotation do not include component deterioration belonging to the detection signals acquired during the period of occurrence of transient response, but include normal components belonging to the detection signals acquired after the period of occurrence of transient response.

Even with such a configuration, the same advantageous effects as those of the above-described embodiment can be achieved.

Fourth Modification

A pair of learning data (input-side and output-side learning data) and input data may be count data (projection data) output from the X-ray detector 18, for example sinogram data. Sinogram data is a map indicating values of projection data of each X-ray detection element, wherein the horizontal axis indicates a location of each X-ray detection element and the vertical axis indicates a view. Alternately, the values of time-series projection data of an X-ray detection element of interest may be included in the sinogram data.

FIG. 6 is a diagram for explaining an example of a machine learning model according to the present modification. In the example shown in FIG. 6, each piece of time-series data (sinogram data) includes time-series data of count values in a first rotation (indicated by the solid line) and time-series data of count values in a second rotation (indicated by the dotted line). The time-series data (a), (b), and (c) respectively indicate time-series data of count values for respective pixels. As shown in FIG. 6, the input-side and output-side learning data is typically sinogram data obtained in a first and a second rotation, respectively. The input data is typically the obtained sinogram data of a first rotation (data targeted for correction).

Herein, the sinogram data acquired in a first rotation is data that includes an influence of a transient response of the X-ray detection elements, which includes component deterioration belonging to projection data acquired during a period in which a transient response occurs, and normal components belonging to the projection data acquired after the period of occurrence of transient response. The sinogram data acquired in a second rotation do not include component deterioration belonging to the projection data acquired during the period of occurrence of transient response, but include normal components belonging to projection data acquired after the period of occurrence of transient response. The count data may be data after preprocessing by the preprocessing function 442.

Specifically, the processing circuitry 44 that enables the model generation function 446 obtains sinogram data (a series of time-series data) from the data acquisition circuitry 18. The processing circuitry 44 generates a set of learning data for each piece of obtained sinogram data. The processing circuitry 44 that enables the transient response correction function 447 obtains sinogram data that includes component deterioration resulting from a transient response of the X-ray detector 12 (data targeted for correction) from the data acquisition circuitry 18 or the preprocessing function 442, and corrects the data using the machine learning model. The processing circuitry 44 that enables the reconstruction processing function 443 generates CT image data based on the corrected sinogram data.

Even with such a configuration, the same advantageous effects as those of the above-described embodiment can be achieved.

Fifth Modification

Data that includes component deterioration resulting from a transient response of the X-ray detector is not limited to data obtained in a first rotation, and it may be data determined in accordance with a predetermined period of time elapsed since the incidence of X-rays started (start of detection), for example. In this case, the input-side learning data and input data (data targeted for correction) is a reconstructed image generated based on the projection data acquired in the predetermined period from the start of X-ray incidence (start of detection). Similarly, the output-side learning data is, for example, a reconstructed image generated based on the projection data acquired after the predetermined period has elapsed since the X-ray detection started. Assume that the input-side learning data, the output-side learning data, and the input data are generated based on the projection data acquired from the same rotation angle and within the same angle range.

The predetermined elapsed time may be determined in accordance with transient response characteristics (a period of occurrence of transient response) of a semiconductor, etc. used in the X-ray detector 12.

There is a case where data obtained in the second rotation or thereafter may be used as data that includes a transient response of the X-ray detector 12. Which data to be used may be determined in accordance with, for example, transient response characteristics (a period of occurrence of transient response) of a semiconductor, etc. used in the X-ray detector 12 or a rotation speed.

When X-rays are generated in a pulse form to obtain scano data, data that includes component deterioration resulting from a transient response of the X-ray detector may be defined not only by the number of rotations or time, but also by how many pulses have occurred.

Even with such a configuration, the same advantageous effects as those of the above-described embodiment can be achieved.

Sixth Modification

The output-side learning data is not limited to data of a second rotation and it may be data of a third rotation or thereafter. Even with such a configuration, the same advantageous effects as those of the above-described embodiment can be achieved.

Seventh Modification

The output-side learning data may further include data of a third rotation or thereafter in addition to data of a second rotation. In other words, as the output-side learning data, data acquired from multiple rotations including the second rotation and thereafter to which a calculation, such as addition or averaging, is applied, may be used. Even with such a configuration, the same advantageous effects as those of the above-described embodiment can be achieved. If the data of a second rotation and thereafter is added, noise can be further effectively reduced.

Eighth Modification

The input-side learning data and the input data may include data of a second rotation and thereafter in addition to the data of a first rotation. For brevity of description, assume that projection data is acquired only from three rotations during CT scanning. In addition, assume that the period of occurrence of transient response is within a period of a first rotation. In this case, the input-side learning data and the input data is generated based on a sum or an average of the data of a first through a third rotation. On the other hand, the output-side data is generated based on a sum or an average of the data of a second and a third rotation, excluding a first rotation. Even with such a configuration, the same advantageous effects as those of the above-described embodiment can be achieved.

Ninth Modification

Figure 7:
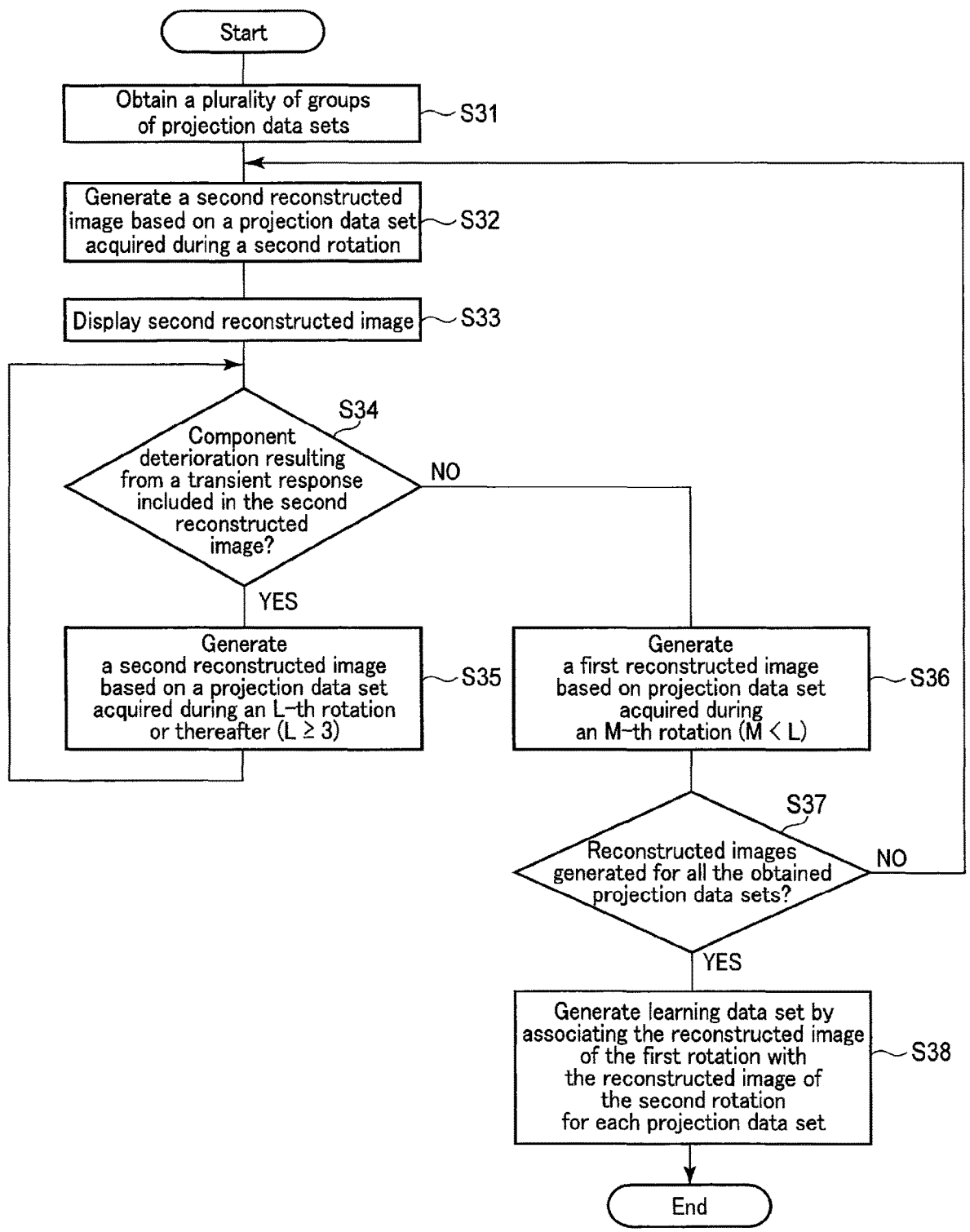
FIG. 7 is a flowchart showing an example of a flow of generation of a learning data set for the machine learning model shown in FIG. 3 according to a ninth modification.

The data of how many rotations have occurred is used as the input-side learning data, the output-side learning data, and the input data respectively may be determined. FIG. 7 is a flowchart showing an example of a flow of generation of learning data sets for the machine learning model shown in FIG. 3 according to the present modification.

In step S31, the processing circuitry 44 that enables the system control function 441 obtains a plurality of groups of projection data sets in a manner similar to step S11 shown in FIG. 4. Each of the groups of projection data sets is an example of a series of time-series data.

In step S32, the processing circuitry 44 that enables the reconstruction processing function 443 generates a reconstructed image of a second rotation (second reconstructed image) based on the projection data set acquired in a second rotation, similarly to step S13 shown in FIG. 4.

In step S33, the processing circuitry 44 that enables the display control function 445 causes the display 42 to display the second reconstructed image generated in step S32.

In step S34, the processing circuitry 44 that enables the model generation function 446 determines whether or not the second reconstructed image includes component deterioration resulting from a transient response based on an output from the input interface 43 in accordance with a user's input, for example. For example, a user, such as a physician, inputs a result of the determination as to whether or not the second reconstructed image includes component deterioration resulting from a transient response in accordance with whether or not an artifact is present in the displayed second reconstructed image. If it is determined that component deterioration resulting from a transient response is included in the second reconstructed image, the flow of FIG. 7 proceeds to step S35; if no such determination is made, the flow proceeds to step S36.

In step S35, the processing circuitry 44 that enables the reconstruction processing function 443 generates a second reconstructed image based on a projection data set acquired in an L-th rotation (L $\geq$ 3) or thereafter. Thereafter, the flow of FIG. 7 proceeds to step S34, and it is determined whether or not the second reconstructed image generated in this step includes component deterioration resulting from the transient response.

In step S36, the processing circuitry 44 that enables the reconstruction processing function 443 generates a reconstructed image (first reconstructed image) based on a projection data set acquired in an M-th rotation (M<L). In this case, the first reconstructed image may be generated based on an average or a sum of the plurality of groups of projection data sets.

In step S37, the processing circuitry 44 that enables the model generation function 446 determines whether or not the reconstructed images have been generated for all the projection data sets in the flow of step S32 through step S36, similarly to step S14 of FIG. 4.

In step S38, the processing circuitry 44 that enables the model generation function 446 generates a learning data set through associating the first reconstructed image (input-side learning data) with the second reconstructed image (output-side learning data) for each projection data set, in a manner similar to step S15 of FIG. 4.

The processing circuitry 44 that enables the model generation function 446 may further determine, for example, whether or not there is projection data that includes component deterioration resulting from a transient response for each of the plurality of groups of projection data sets. In other words, the processing circuitry 44 may further determine, for each of the groups of projection data sets, whether or not projection data acquired during a period of occurrence of transient response is included in the group of projection data sets. This determination may be made based on the reconstructed image, etc. If it is determined that the projection data set does not include component deterioration resulting from a transient response, step S38 is not performed.

Figure 8:
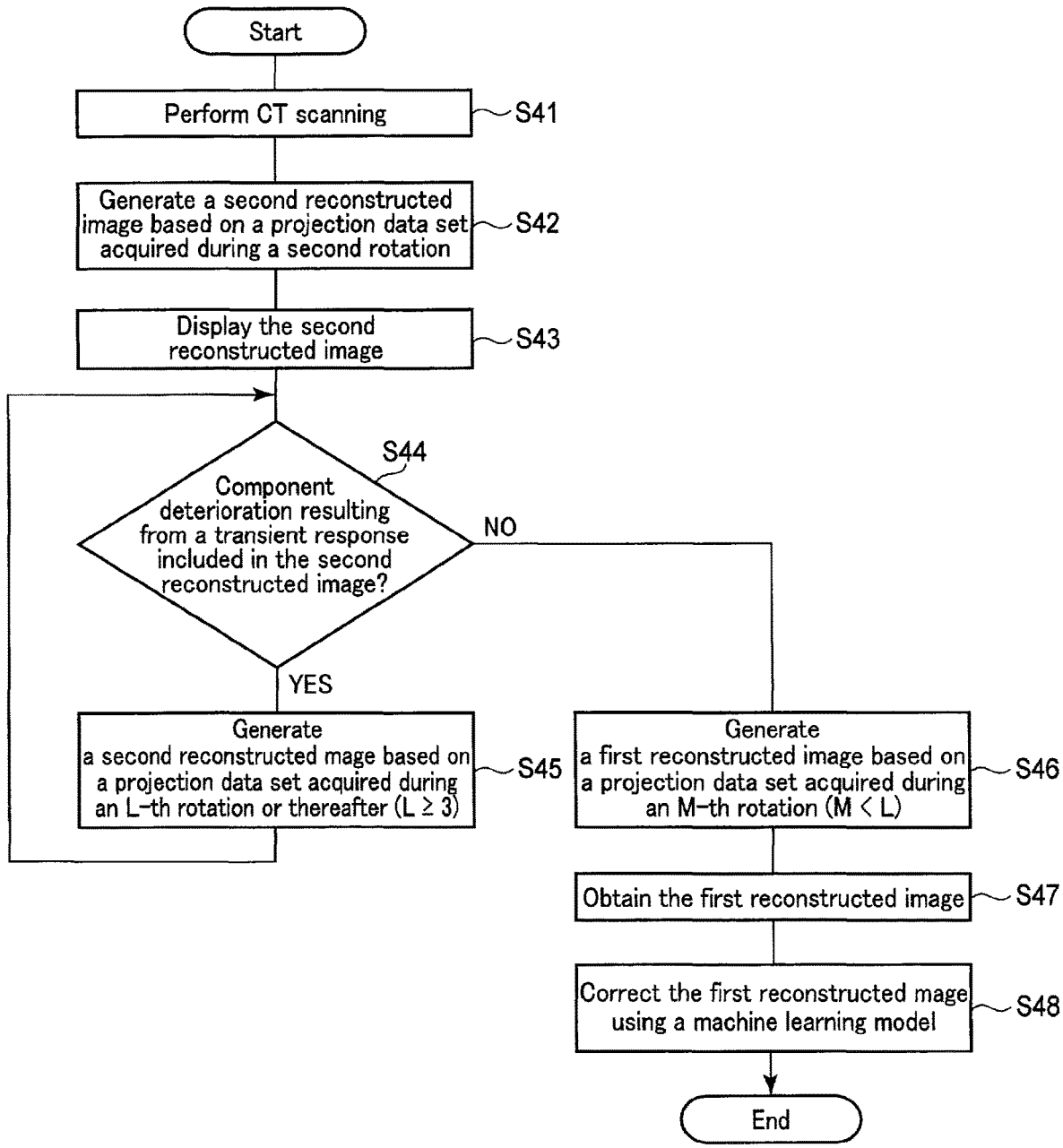
FIG. 8 is a flowchart showing an example of transient response correction using the machine learning model shown in FIG. 3 according to the ninth modification.

FIG. 8 is a flowchart showing an example of transient response correction using the machine learning model shown in FIG. 3 according to the ninth modification.

In step S41, the processing circuitry 44 that enables the system control function 441 performs CT scanning and obtains multiple projection data sets output from the data acquisition circuitry 18 in a manner similar to step S21 shown in FIG. 5.

The flow from step S42 through step S46 is the same as the flow from step S32 through step S36 shown in FIG. 7.

The flow from step S47 through step S48 is the same as the flow from step S23 through step S24 shown in FIG. 5.

The processing circuitry 44 that enables the transient response correction function 447 may further determine, for each projection data set obtained by CT scanning, whether or not projection data that include component deterioration resulting from a transient response is included therein. This determination may be made based on the reconstructed image, etc. If it is determined that there is no projection data that includes component deterioration resulting from a transient response, step S48 is not performed. In other words, with the above-described configuration, normal data that does not include a transient response is excluded from input into a machine learning model.

In the present modification, the example is given where a user determines whether or not component deterioration resulting from a transient response is present based on a displayed reconstructed image; however, the modification is not limited to this example. The display to a user may be, as shown in FIG. 6, in a form of a graph, etc. in which time-series data is comparable between a first rotation and a second rotation, for example. The data displayed in a graph may be time-series data, etc. of detection signals belonging to multiple periods.

With such a configuration, the input-side learning data, the output-side learning data, and the input data can be appropriately determined. In other words, according to a technique according to the present modification, an advantageous effect of improving accuracy in correction can be achieved in addition to the advantageous effects achieved in the foregoing embodiment.

10th Modification

Figure 9:
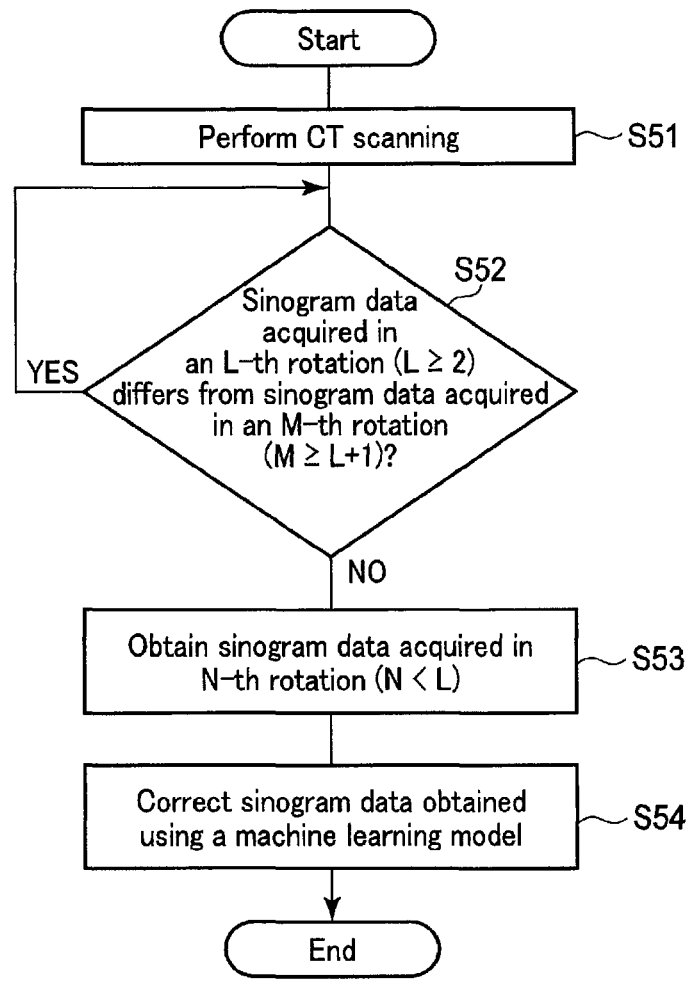
FIG. 9 is a flowchart showing an example of transient response correction using the machine learning model shown in FIG. 3 according to a 10th modification.

The determination of the data of how many rotations have occurred is used as the input-side learning data, the output-side learning data, and the input data respectively, is not necessarily made by a user as in the ninth modification, and it may be made by the processing circuitry 44. FIG. 9 is a flowchart showing an example of transient response correction using the machine learning model shown in FIG. 3 according to the present modification. FIG. 9 indicates an example where sinogram data is used as the input-side learning data, the output-side learning data, and the input data, similarly to the fourth modification. Herein, the flow of the transient response correction is explained; however, the flow of the generation of learning data sets can' be achieved in a similar manner.

In step S51, the processing circuitry 44 that enables the system control function 441 performs CT scanning and obtains multiple projection data sets (sinogram data) output from the data acquisition circuitry 18 in a manner similar to step S21 shown in FIG. 5 and step S41 shown in FIG. 8.

In step S52, the processing circuitry 44 that enables the transient response correction function 447 determines whether or not there is a difference between the sinogram data acquired in the second rotation and the sinogram data acquired in the third rotation. If it is determined that a difference is present, the processing circuitry 44 repeats the comparison of data (for example, comparing the third rotation with the fourth rotation, then the fourth rotation with the fifth rotation, and so on), until no difference is found. The case where it is determined that there is no difference includes a case where the difference is smaller than a predetermined threshold.

In step S53, the processing circuitry 44 that enables the transient response correction function 447 obtains sinogram data to be input (data targeted for correction). Specifically, if it is determined that there is no difference between the third rotation and the fourth rotation in step S52, for example, the processing circuitry 44 obtains sinogram data in the first rotation and/or second rotation as correction target data. Thereafter, in step S54, the processing circuitry 44 corrects the obtained sinogram data, similarly to step S24 of FIG. 5 and step S48 of FIG. 8.

Even with such a configuration, it is possible to appropriately determine each piece of the input-side learning data, the output-side learning data, and the input data. In other words, according to a technique according to the present modification, an advantageous effect is achieved of improving accuracy in correction in addition to the advantageous effects achieved in the foregoing embodiment.

11th Modification

The learning and/or reinforcement learning of the machine-learning model is not necessarily conducted for each imaging condition and imaging target, and the learning may be conducted for multiple imaging conditions and imaging targets. The learning and/or reinforcement learning of the machine learning model may be conducted for each energy bin. The learning and/or reinforcement learning of the machine learning model may be conducted for each X-ray detection element, or for a group of multiple X-ray detection elements.

Figure 10:
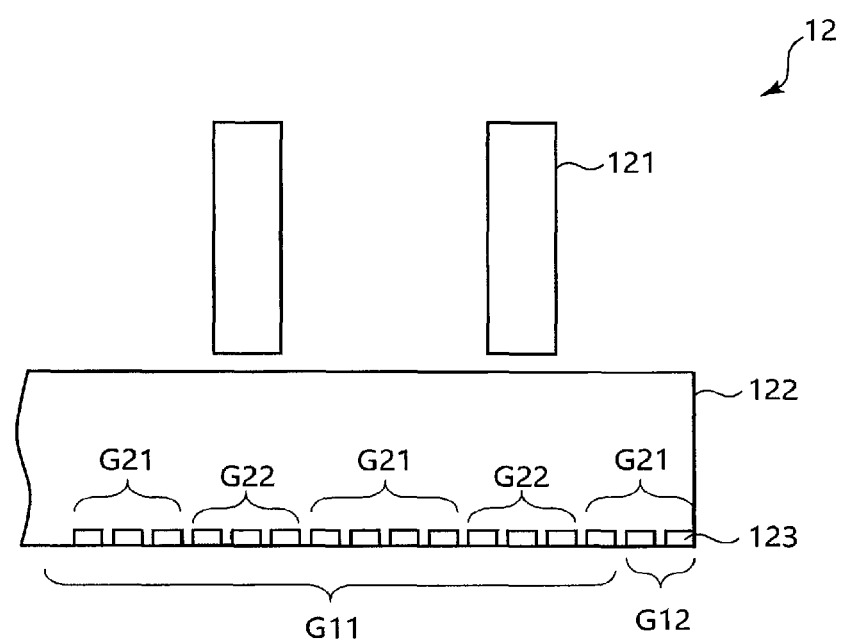
FIG. 10 is a diagram for explaining an example of a unit of learning in a machine learning model according to an 11th modification.

FIG. 10 is a diagram for explaining an example of a unit of learning in a machine learning model according to the 11th modification. For example, in the X-ray detector 12, the X-ray detection elements 123 (pixels) arranged in the center of the compound semiconductor 122 and the X-ray detection elements 123 arranged in the periphery may have different transient response characteristics in some cases. For this reason, as shown in FIG. 10, the learning of a machine learning model may be conducted for each of a group G11 of the X-ray detection elements arranged in the center of the compound semiconductor 122 and a group G12 of the X-ray detection elements arranged in the periphery. In this case, as the transient response characteristics differ between the center and the periphery, different output-side learning data may be used for the center and the periphery. For example, as the output-side learning data, the data of the third rotation is used for the center where an amount of incident X-rays is small, and the data of the second rotation is used for the periphery where an amount of incident X-rays is large.

The learning of the machine learning model may be conducted respectively for, among the plurality of X-ray detection elements 123, a group G21 of the X-ray detection elements not under an influence of the collimator 121 and a group G22 of the X-ray detection elements under an influence of the collimator 121, for example in the shadow of the collimator 121.

The learning of the machine-learning model may be conducted for respective transient response characteristics of the X-ray detection elements 123. For example, the machine learning model may be learned for a group of X-ray detection elements that exhibit overshoot, and a group of X-ray detection elements that exhibit undershoot, respectively. In this case, the X-ray detection elements may be further grouped in accordance with a degree of a transient response.

Transfer learning may be conducted as learning of a machine learning model. For example, the machine learning model may be further individually learned as described in the foregoing embodiment and modifications, after being learned in advance with data relating to the X-ray detectors 12 of multiple apparatuses.

This configuration can achieve an advantageous effect of further improving the accuracy of transient response, in addition to the advantageous effects achieved in the foregoing embodiment.

12th Modification

As the input-side learning data, the output-side learning data, and the input data, not only data of single rotation but data of a half rotation, etc. may be used. In this case, as long as the input-side learning data corresponds to the output-side learning data, the learning data and the input data may be obtained from different angle ranges. Even with such a configuration, the same advantageous effects as those of the above-described embodiment can be achieved.

13th Modification

As the input-side learning data and the output-side learning data, data are obtained through a numerical value simulation (numerical value analysis) using a numerical value phantom. The data obtained through the numerical value simulation may be used only for either one of the input-side or the output side learning data. In this case, as the other learning data, data acquired by measurement under the same condition may be used. The input-side learning data and the output-side learning data may be generated using data acquired for another patient or sample (imaging target). With these configurations, an advantageous effect in easy acquisition of learning data can be achieved, in addition to the advantageous effects described in the foregoing embodiment.

14th Modification

The input-side learning data and the output-side learning data may be data acquired under different dose conditions. For example, as the output-side learning data, measurements of a phantom under the influence of a high dose may be used. This configuration can achieve an advantageous effect of improving the accuracy of noise reduction, in addition to the advantageous effects achieved in the foregoing embodiment.

15th Modification

The machine learning model may be learned with reinforcement, through the use of the obtained correction target data (data that includes component deterioration resulting from a transient response) and the corrected data (data in which component deterioration resulting from a transient response has been reduced). At this time, the output-side learning data, which has been used in the learning or previous reinforcement learning, may be used. With this configuration, an advantageous effect of easy acquisition of learning data and generation of learning data sets can be achieved, in addition to the advantageous effects described in the foregoing embodiment.

16th Modification

The X-ray detector 12 may include a memory 41 storing a machine learning model, and a processing circuitry 44 that enables a transient response correction function. In other words, the X-ray detector 12 may be a detector that outputs data in which an influence of a transient response of the X-ray detection elements has been corrected. At this time, the processing circuitry 44 may be configured to enable the model generation function 446. The memory 41 in which the machine learning model is stored may be provided externally to the X-ray detector 12. Even with these configurations, the same advantageous effects as those of the above-described embodiment can be achieved.

According to at least one of the above-explained embodiment and modifications, it is possible to reduce deteriorations in the output from an X-ray detector resulting from a transient response.

The term "processor" used in the foregoing description means, circuitry, for example, a CPU, a GPU, an application specific integrated circuit (ASIC), or a programmable logic device (PLD). The PLD includes a simple programmable logic device (SPLD), a complex programmable logic device (CPLD), and a field programmable gate array (FPGA). The processor realizes its function by reading and executing the program stored in the storage circuitry. The storage circuitry storing the program thereon is a computer-readable non-transitory storage medium. Instead of storing a program on the storage circuitry, the program may be directly integrated into the circuitry of the processor. In this case, the function is activated by reading and executing the program integrated into the circuitry. The function corresponding to the program may be realized by a combination of logic circuits, and not by executing the program. Each processor of the present embodiment is not limited to a case where each processor is configured as a single circuit; a plurality of independent circuits may be combined into one processor to realize the function of the processor. In addition, a plurality of structural elements in FIG. 1 may be integrated into one processor to realize the function.

The processing circuitry 44 may include a circuitry configuration that enables a function similar to the machine learning model according to the embodiment and/or each modification in which a parameter has been learned such that data that includes component deterioration resulting from a transient response is input and data in which component deterioration resulting from a transient response is reduced is output. For example, such circuitry is achieved by an integrated circuit such as an ASIC or a PLD.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray imaging apparatus, comprising:
an X-ray tube that generates X-rays;
an X-ray detector that detects X-rays generated by the X-ray tube and passing through a subject; and
processing circuitry configured to
obtain correction-target data that includes component deterioration resulting from a transient response of the X-ray detector; and
output corrected data in which the component deterioration resulting from the transient response of the X-ray detector is reduced based on the obtained correction-target data and a model that outputs output data in which the component deterioration resulting from the transient response is reduced based on an input of input data that includes the component deterioration of the transient response.

2. The X-ray imaging apparatus according to claim 1, wherein the input data that includes the component deterioration of the transient response is data relating to a first period that includes a period in which the transient response occurs.

3. The X-ray imaging apparatus according to claim 2, wherein the first period is a predetermined length of time elapsed since the X-ray was incident to X-ray detection elements of the X-ray detector.

4. The X-ray imaging apparatus according to claim 2, further comprising a gantry configured to rotate the X-ray tube, wherein the first period is a period of a first rotation of the X-ray tube.

5. The X-ray imaging apparatus according to claim 1, wherein the input data is a reconstructed image generated based on an output of the X-ray detector.

6. The X-ray imaging apparatus according to claim 1, wherein the input data is time-series data of detection signals output from the X-ray detector.

7. The X-ray imaging apparatus according to claim 1, wherein the input data is sinogram data generated based on an output of the X-ray detector.

8. The X-ray imaging apparatus according to claim 1, wherein the input data is scan data generated based on an output of the X-ray detector.

9. The X-ray imaging apparatus according to claim 1, wherein the model is a machine learning model in which a parameter is learned so that data relating to a first period that includes a period in which the transient response of the X-ray detector occurs and a second period that follows the first period are respectively used as input-side and output-side learning data.

10. The X-ray imaging apparatus according to claim 9, further comprising a gantry configured to rotate the X-ray tube,
wherein the first period and the second period are a period of a first rotation of the X-ray tube and a period of a second rotation or a rotation thereafter of the X-ray tube, respectively.

11. The X-ray imaging apparatus according to claim 9, further comprising a gantry configured to rotate the X-ray tube,
wherein data relating to the second period is a sum or an average of data obtained during a plurality of rotations of the X-ray tube.

12. The X-ray imaging apparatus according to claim 9, wherein
in the machine learning model the parameter is learned for each energy bin of a plurality of energy bins of the detected X-rays detected by the X-ray detector.

13. The X-ray imaging apparatus according to claim 9, wherein:
the X-ray detector has a plurality of X-ray detection elements, and
in the machine learning model the parameter is learned for each group, of a plurality of groups, that includes a set of the plurality of X-ray detection elements.

14. The X-ray imaging apparatus according to claim 13, wherein
the plurality of groups includes a first group relating to a first plurality of X-ray detection elements provided in a periphery of the X-ray detector, and a second group of a second plurality of X-ray detection elements provided in a center of the X-ray detector.

15. The X-ray imaging apparatus according to claim 13, wherein the group is set in accordance with a transient response characteristic of each of the plurality of X-ray detection elements.

16. The X-ray imaging apparatus according to claim 9, wherein in the machine learning model the parameter is learned for multiple imaging conditions and multiple imaging targets.

17. The X-ray imaging apparatus according to claim 9, wherein the learning data includes data generated using a numerical value phantom.

18. A medical image processing apparatus, comprising:
processing circuitry configured to
obtain a series of time-series data that includes component deterioration resulting from a transient response of an X-ray detector;
generate, based on the series of time-series data, first data regarding a first period that includes a period in which the transient response of the X-ray detector occurs and second data regarding a second period that follows the first period; and
output the first data regarding the first period and the second data regarding the second period as learning data used for a learning model that outputs output data in which the component deterioration resulting from the transient response is reduced based on an input of input data that includes the component deterioration resulting from the transient response.

19. An X-ray detector, comprising:
a plurality of X-ray detection elements that detect X-rays generated from an X-ray tube and passing through a subject; and
processing circuitry configured to
obtain correction-target data that includes component deterioration resulting from a transient response of the plurality of X-ray detection elements; and
output corrected data in which the component deterioration resulting from the transient response of the X-ray detection elements is reduced, based on the obtained correction-target data and a model that outputs output data in which the component deterioration resulting from the transient response is reduced based on an input of input data that includes the component deterioration resulting from the transient response.

20. A correction method of an X-ray detector, the method comprising:
obtaining correction-target data that includes component deterioration resulting from a transient response of an X-ray detector; and outputting corrected data in which the component deterioration resulting from the transient response of the X-ray detector is reduced, based on the obtained correction-target data and a model that outputs output data in which the component deterioration resulting from the transient response is reduced based on an input of input data that includes the component deterioration resulting from the transient response.

* * * * *